US012059450B2

(12) United States Patent
Shin et al.

(10) Patent No.: US 12,059,450 B2
(45) Date of Patent: Aug. 13, 2024

(54) ANTICANCER PHARMACEUTICAL COMPOSITION CONTAINING IF1 AS ACTIVE INGREDIENT

(71) Applicants: Korea University Research And Business Foundation, Seoul (KR); CHA UNIVERSITY INDUSTRY-ACADEMIC COOPERATION FOUNDATION, Pocheon-si (KR)

(72) Inventors: Min-Jeong Shin, Seoul (KR); Hyeon Soo Kim, Seoul (KR); Inhyeok Jeong, Goyang-si (KR); Eun Hye Yoo, Seoul (KR); Ji Hyung Chung, Seoul (KR)

(73) Assignees: Korea University Research and Business Foundation, Seoul (KR); CHA UNIVERSITY INDUSTRY—ACADEMIC COOPERATION FOUNDATION, Pocheon-si (KR)

( * ) Notice: Subject to any disclaimer, the term of this patent is extended or adjusted under 35 U.S.C. 154(b) by 535 days.

(21) Appl. No.: 17/281,808

(22) PCT Filed: Oct. 2, 2019

(86) PCT No.: PCT/KR2019/012929
§ 371 (c)(1),
(2) Date: Mar. 31, 2021

(87) PCT Pub. No.: WO2020/071795
PCT Pub. Date: Apr. 9, 2020

(65) Prior Publication Data
US 2021/0386822 A1 Dec. 16, 2021

(30) Foreign Application Priority Data

Oct. 2, 2018 (KR) .................. 10-2018-0117694

(51) Int. Cl.
*A61K 38/17* (2006.01)
*A23L 33/17* (2016.01)
*A61P 35/00* (2006.01)

(52) U.S. Cl.
CPC .......... *A61K 38/1709* (2013.01); *A23L 33/17* (2016.08); *A61P 35/00* (2018.01)

(58) Field of Classification Search
CPC ...... A61K 38/1709; A23L 33/17; A61P 35/00
See application file for complete search history.

(56) References Cited

U.S. PATENT DOCUMENTS

| 5,240,714 A * | 8/1993 | Rof ........................... A61P 7/10 424/545 |
| 2003/0026781 A1* | 2/2003 | Anderson ............... C12N 15/62 424/85.5 |
| 2004/0072739 A1* | 4/2004 | Anderson ............... C12N 15/62 514/6.9 |
| 2006/0135468 A1* | 6/2006 | Khodadoust ......... A61K 31/505 514/183 |
| 2010/0190845 A1* | 7/2010 | Juan ........................ A61P 35/00 514/460 |
| 2013/0172266 A1* | 7/2013 | Kelley ................... A61K 47/64 514/21.7 |
| 2015/0064714 A1* | 3/2015 | Andrianaivomananjaona ............. G01N 33/6896 530/324 |
| 2015/0065556 A1* | 3/2015 | Birsoy ............... G01N 33/6896 435/6.12 |
| 2018/0143199 A1 | 5/2018 | Liu et al. |

FOREIGN PATENT DOCUMENTS

| JP | 2003-527835 A | 9/2003 |
| KR | 10-2018-0033108 A | 4/2018 |
| WO | 98/33909 A1 | 8/1998 |
| WO | 01/34833 A2 | 5/2001 |
| WO | 2018/134265 A1 | 7/2018 |
| WO | WO-2018134265 A1 * | 7/2018 .............. A61P 35/00 |

OTHER PUBLICATIONS

Garcia-Ledo et al., 2017, Overexpression of the ATPase Inhibitory Factor 1 Favors a Non-metastatic Phenotype in Breast Cancer, Frontiers in Oncology, 7: 69 (13 pages).*
Garcia-Bermudez et al., 2016, The ATPase Inhibitory Factor 1 (IF1): A master regulator of energy metabolism and of cell survival, Biochimica et Biophysica Acta, 1857: 1167-1182.*
Domenis et al., 2011, Mitochondrial bioenergetic profile and responses to metabolic inhibition in human hepatocarcinoma cell lines with distinct differentiation characteristics, J Bioenerg Biomembr, 43: 493-505.*
Santacatterina et al., 2015, Down-regulation of oxidative phosphorylation in the liver by expression of the ATPase inhibitory factor 1 induces a tumor-promoter metabolic state, Oncotarget, 7(1): 490-508.*
Hardonniere et al., 2017, Role for the ATPase inhibitory factor 1 in the environmental carcinogen-induced Warburg phenotype, Scientific Reports, 7: 195 (12 pages).*
Zhao et al., 2016, Expression of ATPase inhibitory factor 1 in normal and pathological tissues of female reproductive system, J South Med Univ, 36(12): 1626-1631.*
Communication dated Jul. 25, 2023 issued by the State Intellectual Property Office of the P.R.China in application No. 201980079394. 5.
M Sanchez-Arago, et al., "Expression, regulation and clinical relevance of the ATPase inhibitory factor 1 in human cancers", Oncogenesis, 2013, vol. 2, article No. e46; pp. 1-11.

(Continued)

*Primary Examiner* — Amber D Steele
(74) *Attorney, Agent, or Firm* — Sughrue Mion, PLLC (57) ABSTRACT

The present invention pertains to an anticancer composition containing IF1 (ATPase inhibitory factor 1). The IF1 (ATPase inhibitory factor 1) according to the present invention has the effect of releasing extracellular ATP, induces cytotoxicity in various cancer cells and exhibits anticancer efficacy, and is thus very useful as an active ingredient of a powerful anticancer agent.

2 Claims, 6 Drawing Sheets

Specification includes a Sequence Listing.

(56) References Cited

OTHER PUBLICATIONS

Nick R. Burwick, et al., An inhibitor of the F1 subunit of ATP synthase (IF1) modulates the activity of angiostatin on the endothelial cell surface1, Journal of Biological Chemistry, Jan. 21, 2005, vol. 280, No. 3, (1740-1745), pp. 1-18.
G. Sgarbi, et al., "The role of the ATPase inhibitor factor 1 (IF1) in cancer cells adaptation to hypoxia and anoxia", Biochimica et Biophysica Acta (BBA)—Bioenergetics, 2018 (Electronic publication Oct. 31, 2017), vol. 1859, pp. 99-109.
Pau B. Esparza-Molto, et al., "The Role of Mitochondrial H+-ATP Synthase in Cancer", Frontiers in Oncology, Mar. 7, 2018, vol. 8, article No. 53, pp. 1-8.
Michelangelo Campanella, et al., "Regulation of Mitochondrial Structure and Function by the F1Fo-ATPase Inhibitor Protein, IF1", Cell Metabolism, Jul. 2008, vol. 8, pp. 13-25.
Laura Sanchez-Cenizo, et al., "Up-regulation of the ATPase Inhibitory Factor 1 (IF1) of the Mitochondrial H+-ATP Synthase in Human Tumors Mediates the Metabolic Shift of Cancer Cells to a Warburg Phenotype", The Journal of Biological Chemistry, Aug. 13, 2010, vol. 285, No. 33, pp. 25308-25313.
Annina Lyly, et al., "Deficiency of the INCL protein Ppt1 results in changes in ectopic F1-ATP synthase and altered cholesterol metabolism", Human Molecular Genetics, 2008, vol. 17, No. 10, pp. 1406-1417.
Alessandra Piccini, et al., "ATP is released by monocytes stimulated with pathogen-sensing receptor ligands and induces IL-1B and IL-18 secretion in an autocrine way", PNAS, Jun. 10, 2008, vol. 105, No. 23, pp. 8067-8072.
International Search Report for PCT/KR2019/012929 dated Jan. 10, 2020 (PCT/ISA/210).
Genbank, Mus musculus ATPase inhibitory factor 1 (Atpif1), mRNA, NCBI Reference Sequence: NM_007512.3, 2015 [retrieved from internet on May 28, 2021: htttps://www.ncbi.nlm.nih.gov/nuccore/NM_007512.3/] (3 pages).
Communication dated Apr. 7, 2021, issued by the Korean Intellectual Property Office in application No. 10-2019-0116680.
Xuemei Ding et al., "ATPase inhibitory factor 1 inhibition improves the antitumor of YC-1 against hepatocellular carcinoma", Oncology Letters, vol. 16: pp. 5230-5236, 2018 (7 pages).
Tao Yin et al., "ATPase inhibitory factor 1 is a prognostic marker and contributes to proliferation and invasion of human gastric cancer cells", Biomedicine & Pharmacotherapy, vol. 70, 2015, pp. 90-96 (7 pages).

* cited by examiner

ANTICANCER PHARMACEUTICAL COMPOSITION CONTAINING IF1 AS ACTIVE INGREDIENT

CROSS REFERENCE TO RELATED APPLICATIONS

This application is a National Stage of International Application No. PCT/KR2019/012929 filed Oct. 2, 2019, claiming priority based on Korean Patent Application No. 10-2018-0117694 filed Oct. 2, 2018, the entire disclosures of which are incorporated herein by reference.

TECHNICAL FIELD

The present invention relates to a composition for providing anti-cancer activity or inhibiting cancer metastasis comprising IF1 (ATPase inhibitory factor 1), and more particularly to a pharmaceutical composition or food for providing anti-cancer activity or inhibiting cancer metastasis comprising, as an active ingredient, IF1, having effects of inhibiting proliferation of cancer cells, increasing extracellular ATP release, suppressing migration of cancer cells, and inducing cancer apoptosis or autophagy of cancer cells.

BACKGROUND ART

The global cancer incidence rate is increasing by more than 5% annually due to serious environmental problems and the increasing elderly population. In recent years, deaths from cancer have accounted for about 1 in 4 of all deaths, and this trend is increasing. Carcinogens that cause cancer include smoking, ultraviolet rays, chemicals, food, and other environmental factors. However, it is difficult to develop therapeutic agents due to the wide variety of causes thereof, and the effect of a therapeutic agent also varies depending on the site of occurrence.

Currently, surgical therapy, chemotherapy, biotherapy, radiation therapy and the like are used for cancer treatment. Chemotherapy is also referred to as drug therapy, and uses synthesized chemicals such as nucleic-acid-alkylating agents, metabolic antagonists, natural products, and hormones, and biotherapy prevents the progression of cancer by weakening the activity of cancer cells by restoring or improving the immune function of the human body. Cytokines, immunotherapy drugs, gene therapeutic drugs, cancer vaccines, angiogenesis inhibitors, and the like are available.

To date, these methods have been applied singly or in combination to treatment, but the substances used as therapeutic agents are highly toxic, and moreover, due to side effects, drug resistance, and recurrence, there is no perfect treatment. Therefore, there is an urgent need to develop an anticancer agent that selectively can remove only cancer cells, prevent the occurrence of cancer and treat cancer, and is less toxic and is effective.

Meanwhile, IF1 is a major protein that interferes with the function of ATPase, and many studies have been conducted thereon as a target that is naturally produced in the human body and regulates ATP production and degradation through mitochondria (Campanella et al., *Cell Metab*, 8:13-25, 2008). IF1 is overexpressed in various cells and cancer cells corresponding thereto, but the pattern is different for each cell line. This implies that the effects of IF1 on the human body may vary in a tissue-specific manner. The results of previous studies using antibodies targeting the IF1 protein showed expression of high levels of IF1 in epithelial cells of the stomach, heart, liver, endometrium and kidneys. Unlike this, IF1 levels in gastric, pulmonary, breast, colonic and ovarian cells tended to increase significantly in cancer cells compared to normal cells. However, the expression level of IF1 at the gene level did not show the same behavior as above. In the colon and breast, the expression level of IF1 mRNA in cancer cells was increased compared to that of normal cells, but in the lungs and ovaries, the expression level was higher in normal cells (Maria et al., *Oncogenesis* 2.4: e46, 2013; Laura, et al., *Journal of Biological Chemistry*, jbc-M110, 2010)

In addition, ATPase, which is a target of IF1, has been reported to be expressed in cell membranes of various cell types as well as in the mitochondria. Specifically, ATPase is present in HUVEC, BCE (Bos taurus eye), A549 (lung carcinoma), SNU-C5 (human stomach), THP-1 (monocytic cell), HepG2 (liver), CEM (human leukemia cells), BAEC (bovine aortic endothelial cells), amygdala, neuroblastoma B103, C6 astrocytoma, Daudi (human lymphoma), fibroblast, MOLT-4 T cells, 3T3-L1, HaCaT (immortal keratinocyte), breast cancer, 143B (osteosarcoma), 293T (kidney), heart, spleen, thymus, and skeletal muscle (Lyly, Annina, et al., *Human molecular genetics* 17.10: 1406-1417, 2008). Since all of the cell lines and tissues described above have different subunits of ATPase, the injection of IF1 will affect changes in the function of each tissue in the human body. In other words, IF1 binds to F1-ATPase in the cell membrane and inhibits the degradation of ATP by the enzyme, resulting in an increase in the amount of extracellular ATP (exATP), and the increased exATP can be expected to exert a prophylactic or therapeutic effect on cancer through a mechanism that triggers related purine signaling.

Accordingly, as a result of extensive efforts to develop therapeutic agents for cancer that do not have side effects but exhibit excellent effects, the present inventors found that IF1 recombinant proteins have effects of inhibiting proliferation of cancer cells, increasing extracellular ATP release, inhibiting migration of cancer cells, and inducing apoptosis or autophagy of cancer cells in a variety of cancer cells. Based on this finding, the present invention was completed.

DISCLOSURE

Technical Problem

Therefore, the present invention has been made in view of the above problems, and it is one object of the present invention to provide a pharmaceutical composition or food for providing anti-cancer activity or inhibiting cancer metastasis comprising, as an active ingredient, IF1, having effects of activating the immune system, providing anti-cancer activity and inhibiting cancer metastasis by inhibiting proliferation of cancer cells, increasing extracellular ATP release, suppressing migration of cancer cells, and inducing apoptosis (cell death) or autophagy of cancer cells.

Technical Solution

In accordance with one aspect of the present invention, the above and other objects can be accomplished by the provision of a pharmaceutical composition for providing anti-cancer activity or inhibiting cancer metastasis containing IF1 (ATPase inhibitory factor 1) as an active ingredient.

In accordance with another aspect of the present invention, provided is a functional food for providing anti-cancer activity or inhibiting cancer metastasis containing IF1 (ATPase inhibitory factor 1) as an active ingredient.

In accordance with another aspect of the present invention, provided is a method for preventing or treating cancer or inhibiting cancer metastasis comprising administering IF1 (ATPase inhibitory factor 1) to a subject.

In accordance with another aspect of the present invention, provided is the use of IF1 (ATPase inhibitory factor 1) for the prevention or treatment of cancer or inhibition of cancer metastasis.

In accordance with another aspect of the present invention, provided is the use of a pharmaceutical composition comprising as an active ingredient IF1 (ATPase inhibitory factor 1) for the prevention or treatment of cancer or inhibition of cancer metastasis.

In accordance with another aspect of the present invention, provided is the use of IF1 (ATPase inhibitory factor 1) for the manufacture of a medicine for preventing or treating cancer or inhibiting cancer metastasis.

BEST MODE

Unless defined otherwise, all technical and scientific terms used herein have the same meanings as appreciated by those skilled in the field to which the present invention pertains. In general, the nomenclature used herein is well-known in the art and is ordinarily used.

ATPase inhibitory factor 1 (hereinafter, referred to as "IF1") is a 9.6-kDa basic protein consisting of 84 amino acids, and is encoded by the ATP5IF1 gene. ATPase consists of F0 and F1 domains and central and peripheral stalks, and is subdivided into multiple subunits. IF1 binds to the F1Fo ATP synthase (multi-subunit, membrane-bound assembly) involved in the synthesis and degradation of ATP in the mitochondria. IF1 binds to the F1-ATPase subunit located in the plasma membrane. At this time, ATP hydrolysis is inhibited by the regulation of F1-ATPase activity, causing an increase in extracellular ATP (exATP). IF1 binds to F1Fo ATP synthase during hypoxia and inhibits ATP degradation, thereby preventing ATP loss and thus inhibiting apoptosis. In addition, it is known that overexpression of endogenous IF1 and reduction of expression of F1Fo ATP synthase observed in cancer cells and the like contributes to energy metabolism reprogramming such as increased glycolysis. As described above, overexpression of IF1 and reduction of expression of F1Fo ATP synthase is observed in diseases with mitochondrial hypofunction as pathophysiology, but there is no known mechanism for preventing or treating cancer by injection of IF1 from an external source.

Immunity improvement plays an important role in mechanisms for preventing cancer, and the increase in exATP by IF1 is expected to play a pivotal role in the activation of the immune system. The increased exATP concentration acts like a danger signal in the human body, causing phagocytosis through the activity of the P2Y2 receptor of monocytes or activating the immune system using Toll-like receptors (TLRs) or NOD-like receptors (NLRs). Regarding inflammasome recruitment, activation of inflammasome by purine signaling through NLRP3 (or NALP3) P2X7, a downstream thereof has been observed, which induces caspase-1 dependent maturation of pro-inflammatory cytokines such as IL-1β through the innate immune system (Piccini, Alessandra, et al., *PNAS* 105.23: 8067-8072, 2008). Therefore, it can be seen that the injection of IF1 from outside functions to regulate the immune system through the release of ATP from the cell membrane of the corresponding cell, performing both paracrine and autocrine functions. Since the proliferation of immune cells, B cells, migration of NK cells, and immune responses of T cells are also regulated by exATP, treatment with IF1 is expected to prevent various carcinomas that use the immune response as a mechanism and to enable the purine system signaling to have a beneficial effect on cancer treatment using the immune system.

Accordingly, in the present invention, a recombinant protein (SEQ ID NO: 1) including GST-tag is produced by cloning the DNA data of IF1 based on the entire mouse IF1 mRNA sequence (NCBI No. NM_007512.3), and some cancer cell lines (liver cancer cell line, HepG2; breast cancer cell line, MDA-MB-231, T47D; cervical cancer cell line, HeLa) were treated with recombinant IF1 to determine the inhibition of proliferation and apoptosis of cancer cells. In addition, it was demonstrated that the ATP concentration in a medium was significantly increased and the migration of cancer cells was inhibited after treatment of cancer cells with IF1.

Therefore, in one aspect, the present invention is directed to a pharmaceutical composition for providing anti-cancer activity or inhibiting cancer metastasis containing IF1 (ATPase inhibitory factor 1) as an active ingredient.

As used herein, the term "anti-cancer" includes "prevention" and "treatment", and the term "prevention" refers to any action that can suppress or delay the onset of cancer by administration of the pharmaceutical composition according to the present invention. As used herein, the term "treatment" or "therapeutic" refers to any action that can ameliorate or beneficially alter the symptoms of cancer by administration of the pharmaceutical composition according to the present invention.

As used herein, the term "metastasis" refers to a state in which a cancer or malignant tumor spreads from the organ where it developed to another tissue spaced apart therefrom.

In the present invention, the IF1 exhibits anti-cancer activity or cancer metastasis inhibitory activity by inhibiting the proliferation of cancer cells, increasing the release of extracellular ATP of cancer cells, inhibiting the migration of cancer cells, or inducing apoptosis or autophagy of cancer cells. It can be seen that the extracellular release of the ATP exhibits anticancer activity by activating the immune system.

In the present invention, the cancer includes general cancer diseases and is preferably selected from the group consisting of liver cancer, breast cancer, uterine cancer, cervical cancer, lung cancer, non-small cell lung cancer, colorectal cancer, prostate cancer, pancreatic cancer, gastric cancer, esophageal cancer, ovarian cancer, bone cancer, adenocarcinoma, bladder cancer, kidney cancer, ureter cancer, bronchial cancer, nasopharyngeal cancer, laryngeal cancer, brain tumors, spinal cord tumors, blood cancer, rectal cancer, skin cancer, head cancer, head and neck cancer, melanoma, small intestine cancer, colon cancer, anal cancer, fallopian tube carcinoma, endometrial cancer, vaginal cancer, vulvar cancer, Hodgkin's disease, lymph adenocarcinoma, gallbladder cancer, endocrine adenocarcinoma, adrenal cancer, soft tissue sarcoma, urethral cancer, penile cancer, chronic or acute leukemia, lymphocytic lymphoma, renal pelvic cancer, brain cancer, central nervous system (CNS) tumors, brainstem glioma and pituitary adenoma, but is not limited thereto.

The pharmaceutical composition of the present invention may be administered in a pharmaceutically effective amount. The term "pharmaceutically effective amount" used herein means an amount sufficient to treat or prevent a disease at a reasonable benefit/risk ratio applicable to medical treatment or prevention. The effective amount is determined depending on factors including the severity of the disease, the activity of the drug, the age, weight, health and gender of the patient, the sensitivity of the patient to the drug, the time of administration, the route of administration, and the rate of excretion and treatment period of the composition of the present invention used, drugs used in combination with or concurrently with the composition of the present invention, and other factors well known in the pharmaceutical field.

The pharmaceutical composition of the present invention may be administered as a single therapeutic agent or in combination with other therapeutic agents, either sequentially or simultaneously. The pharmaceutical composition of the present invention may be administered in single or multiple doses. Taking into consideration these factors, it is important to administer the composition in the minimum amount sufficient to achieve maximum efficacy without side effects.

In addition, the dosage (administered amount) of the pharmaceutical composition according to the present invention may be determined by those skilled in the art in consideration of the purpose of use, the severity of the disease, the patient's age, weight, gender and history, the type of substances used as active ingredients and the like. For example, the pharmaceutical composition may be administered to an adult in a daily dose of 10 mg/kg to 100 mg/kg, more preferably 10 mg/kg to 30 mg/kg. The frequency of administration of the composition of the present invention is not particularly limited, and the composition may be administered one to three times a day, or may be divided into multiple doses and administered throughout the day.

The pharmaceutical composition of the present invention may be prepared in the form of a pharmaceutical composition for treating or preventing cancer, which further contains an appropriate carrier, excipient or diluent commonly used in the preparation of pharmaceutical compositions, and the carrier may include a non-naturally occurring carrier.

Specifically, the pharmaceutical composition may be formulated according to a conventional method in the form of an oral formulation such as a powder, granule, tablet, capsule, suspension, emulsion, syrup or aerosol, an external preparation, a suppository, or a sterile injectable solution.

Specific examples of the carrier, excipient or diluent included in the pharmaceutical composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil and the like. In the case of formulation, the pharmaceutical composition may be prepared using a diluent or excipient such as a commonly used filler, extender, binder, wetting agent, disintegrant or surfactant.

Solid formulations for oral administration may include tablets, pills, powders, granules, capsules and the like, and may be prepared by mixing at least one excipient, for example, starch, calcium carbonate, sucrose, lactose, gelatin or the like. In addition to simple excipients, lubricants such as magnesium stearate and talc are also used.

Liquid formulations for oral administration may be suspensions, oral liquids and solutions, emulsions, syrups and the like, and may contain various excipients such as wetting agents, sweeteners, fragrances, preservatives and the like, in addition to water and liquid paraffin, which are simple diluents that are commonly used. Formulations for parenteral administration may include sterilized aqueous solutions, non-aqueous solvents, suspensions, emulsions, freeze-dried preparations, and suppositories. Examples of non-aqueous solvents and suspensions include propylene glycol, polyethylene glycol, vegetable oil such as olive oil, injectable esters such as ethyl oleate, and the like.

The pharmaceutical composition may be in the form of a sterile injectable preparation such as a sterile injectable aqueous or oily suspension. Such a suspension may be formulated according to techniques known in the art using a suitable dispersing or wetting agent (e.g., Tween 80) and a suspending agent. The sterile injectable preparation may also be a sterile injectable solution or suspension (e.g., a solution in 1,3-butanediol) in a nontoxic parenterally acceptable diluent or solvent. Available acceptable vehicles and solvents may include mannitol, water, Ringer's solution and isotonic sodium chloride solutions. In addition, sterile non-volatile oils are commonly used as solvents or suspension media. For this purpose, any less irritating nonvolatile oil containing synthetic mono- or di-glycerides may also be used. Fatty acids such as oleic acid and glyceride derivatives thereof are useful for injectable preparations, like pharmaceutically acceptable natural oils (e.g., olive oil or castor oil), particularly polyoxyethylated forms thereof.

The pharmaceutical compositions of the present invention may also be administered in the form of a suppository for rectal administration. These compositions can be prepared by mixing the compound of the present invention with suitable non-irritating excipients which are solid at room temperature but liquid at a rectal temperature. Such materials include, but are not limited to, cocoa butter, beeswax and polyethylene glycols.

Parenteral administration of the pharmaceutical composition according to the present invention is particularly useful when the desired treatment relates to a site or organ that is easily accessible by topical application. When applied topically to the skin, the pharmaceutical composition should be formulated in a suitable ointment containing the active ingredient suspended or dissolved in a carrier. The carrier for topical administration of the compound of the present invention includes, but is not limited to, mineral oil, liquid paraffin, white Vaseline, propylene glycol, polyoxyethylene, polyoxypropylene compounds, emulsifying wax and water. Alternatively, the pharmaceutical composition may be formulated in a suitable lotion or cream containing the active compound suspended or dissolved in a carrier. The suitable carrier includes, but is not limited to, mineral oil, sorbitan monostearate, polysorbate 60, cetyl ester wax, cetearyl alcohol, 2-octyldodecanol, benzyl alcohol and water. The pharmaceutical composition of the present invention can also be applied topically in the form of a rectal suppository or suitable enema to the lower intestine. Topically applied transdermal patches also fall within the scope of the present invention.

The pharmaceutical composition of the present invention can be administered as a nasal aerosol or through inhalation. Such a composition is prepared according to techniques well-known in the pharmaceutical field and is prepared as a solution in saline using benzyl alcohol or other suitable preservatives, absorption accelerators to enhance bioavailability, fluorocarbons and/or other solubilizers or dispersants known in the art.

The content of the agent included in the pharmaceutical composition of the present invention is not particularly limited thereto, but may be 0.0001 to 50% by weight, more preferably 0.01 to 10% by weight, based on the total weight of the final composition.

In another aspect, the present invention is directed to a method for preventing or treating cancer or inhibiting cancer metastasis comprising administering IF1 (ATPase inhibitory factor 1) to a subject.

In another aspect, the present invention is directed to the use of IF1 (ATPase inhibitory factor 1) for the prevention or treatment of cancer or inhibition of cancer metastasis.

In another aspect, the present invention is directed to the use of a pharmaceutical composition comprising as an active ingredient IF1 (ATPase inhibitory factor 1) for the prevention or treatment of cancer or inhibition of cancer metastasis.

In another aspect, the present invention is directed to the use of IF1 (ATPase inhibitory factor 1) for the preparation of a drug for preventing or treating cancer or inhibiting cancer metastasis.

As used herein, the term "subject" refers to any animal, including a human, that suffers from or is at risk of developing cancer, and the disease can be effectively prevented or treated by administering the composition according to the present invention thereto.

The cancer treatment is applicable to any mammal that may be afflicted with cancer, including, but not limited to, humans and primates, as well as domestic animals such as cattle, pigs, sheep, horses, dogs and cats, but preferably humans.

As used herein, the term "administration" refers to an action of introducing the pharmaceutical composition according to the present invention into a subject by any appropriate method, and the route of administration of the composition may be any general route, so long as it enables the composition to be delivered to a target tissue. The pharmaceutical composition may be administered intraperitoneally, intravenously, intramuscularly, subcutaneously, intradermally, orally, topically, intranasally, intrapulmonarily or rectally, but is not limited thereto.

In another aspect, the present invention is directed to a functional food for providing anti-cancer activity or inhibiting cancer metastasis containing IF1 (ATPase inhibitory factor 1) as an active ingredient.

As used herein, the term "anti-cancer" includes "prevention" and "amelioration", and the term "prevention" refers to any action that can suppress or delay the onset of cancer by administration of the pharmaceutical composition according to the present invention. As used herein, the term "amelioration" refers to any action that at least reduces the severity of the parameters associated with the condition to be treated, e.g. the severity of symptoms.

As used herein, the term "metastasis" refers to a state in which cancer or a malignant tumor spreads from the organ where it developed to another tissue spaced apart therefrom.

In the present invention, the IF1 exhibits anti-cancer activity or cancer metastasis inhibitory activity by inhibiting the proliferation of cancer cells, increasing the release of extracellular ATP of cancer cells, inhibiting the migration of cancer cells, or inducing apoptosis or autophagy of cancer cells. It can be seen that the extracellular release of the ATP exhibits anticancer activity by activating the immune system.

In the present invention, the cancer includes a general cancer disease and is preferably selected from the group consisting of liver cancer, breast cancer, uterine cancer, cervical cancer, lung cancer, non-small cell lung cancer, colorectal cancer, prostate cancer, pancreatic cancer, gastric cancer, esophageal cancer, ovarian cancer, bone cancer, adenocarcinoma, bladder cancer, kidney cancer, ureter cancer, bronchial cancer, nasopharyngeal cancer, laryngeal cancer, brain tumor, spinal cord tumor, blood cancer, rectal cancer, skin cancer, head cancer, head and neck cancer, melanoma, small intestine cancer, colon cancer, anal cancer, fallopian tube carcinoma, endometrial cancer, vaginal cancer, vulvar cancer, Hodgkin's disease, lymph adenocarcinoma, gallbladder cancer, endocrine adenocarcinoma, adrenal cancer, soft tissue sarcoma, urethral cancer, penile cancer, chronic or acute leukemia, lymphocytic lymphoma, renal pelvic cancer, brain cancer, central nervous system (CNS) tumors, brainstem glioma and pituitary adenoma, but is not limited thereto.

As used herein, the term "functional food" refers to a group of foods that are imparted with an added value using physical, biochemical, and biotechnological techniques, etc. to act and express the functions of the food for a specific purpose, or a food that is designed and processed to sufficiently express body control functions of a food composition, such as bio-defense rhythm control, disease prevention and disease recovery in the body, and specifically, the functional food may be a health functional food.

When the food composition of the present invention is used as a food additive, the food composition may be used alone or in combination with other food or food additives, and can be suitably used in accordance with a conventional method. In general, when preparing food or a beverage, the composition of the present invention is added in an amount of 15% by weight or less, preferably 10% by weight or less, based on the raw material. However, in the case of long-term intake for the purpose of health and hygiene or for the purpose of health management, the amount may be below the range defined above, but it will be obvious that the active ingredient may be used in an amount exceeding the above range because there is no problem in terms of safety.

The food of the present invention may be prepared in any form such as a functional food, nutritional supplement, health food or food additive. For example, the composition of the present invention as a health food may be prepared in the form of a tea, juice or beverage for drinking, or may be granulated, encapsulated and powdered for ingestion. In addition, functional foods may be prepared by adding the composition of the present invention to beverages (including alcoholic beverages), fruits and processed foods thereof (e.g., canned fruit, bottled fruit, jam, marmalade, etc.), fish, meat and processed foods thereof (e.g., ham, sausage, corned beef, etc.), bread and noodles (e.g. udong, soba, ramen, spaghetti, macaroni, etc.), fruit juices, various drinks, cookies, Yeot (Korean hard taffy), dairy products (e.g. butter, cheese, etc.), edible vegetable oils, margarine, vegetable protein, food contained in a retort pouch, frozen food, various seasonings (e.g., miso, soy sauce, sauce, etc.), and the like.

The health functional food includes, as food compositions, various forms such as functional foods, nutritional supplements, health foods, food additives, etc., and the health functional food may be provided by preparing the composition of the present invention in various forms, such as teas, juices or drinks, or performing granulation, encapsulation, or powderization, or by adding these compounds or extracts to various foods such as beverages, fruits and processed foods, fish, meat and processed foods, breads, noodles, seasonings and the like according to conventional methods known in the art.

The health beverage composition may contain additional ingredients such as various flavors or natural carbohydrates, like general beverages. The natural carbohydrates include monosaccharides such as glucose and fructose, disaccharides such as maltose and sucrose, and natural sweeteners such as dextrin and cyclodextrin. In addition, synthetic sweeteners such as saccharin and aspartame may be used. The proportion of the natural carbohydrate can be appropriately selected by those skilled in the art.

In addition to the ingredients described above, the composition of the present invention may contain various nutrients, vitamins, electrolytes, flavoring agents, colorants, pectic acids and salts thereof, alginic acid and salts thereof, organic acids, protective colloidal thickeners, pH adjusters, stabilizers, preservatives, glycerin, alcohols, carbonating agents used in carbonated beverages, and the like. In addition, the composition of the present invention may contain pulp for the production of natural fruit juices, fruit juice beverages and vegetable beverages. These components may be used alone or in combination. The proportion of these additives can also be appropriately selected by those skilled in the art.

EXAMPLE

Hereinafter, the present invention will be described in more detail with reference to examples. However, it will be obvious to those skilled in the art that these examples are provided only for illustration of the present invention and should not be construed as limiting the scope of the present invention based on subject matter of the present invention.

Example 1

Measurement of Extracellular ATP Release

Breast cancer (MDA-MB-231, MCF7, T47D), liver cancer (HepG2), and cervical cancer (HeLa) cell lines were incubated in a DMEM medium containing 10% FBS and 1% penicillin/streptomycin in an incubator at 37° C. under 5% carbon dioxide.

The extracellular ATP release upon treatment with IF1 was measured using a CellTiter-Glo Luminescent Assay kit (Promega, Madison, WI, USA). HepG2 (liver cancer cell line) or MDA-MB-231 (breast cancer cell line) cells ($3\times10^4$ cells/well) were treated with IF1 (100 ng/mL) and then incubated in 1% BSA/DMEM medium in an incubator under conditions of 37° C. and 5% $CO_2$ for 10 seconds, 30 seconds, 1 minute, 5 minutes, 10 minutes and 30 minutes. Then, each medium was harvested and a luminescent assay was performed.

Figure 1:
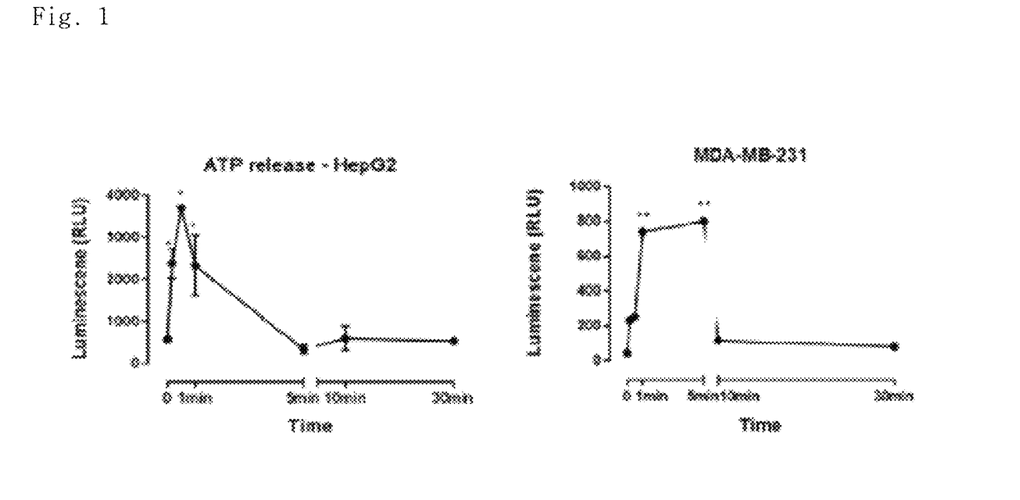
FIG. 1 shows the increase in extracellular ATP release in liver cancer and breast cancer cell lines after IF1 treatment. *p<0.01 is satisfied upon comparison with a basal level.

As a result, it could be seen that the ATP concentration rapidly increased in the medium upon treatment with IF1 (FIG. 1). It can be seen that this increase returned to the basal level after a duration of about 5 minutes in the case of HepG2 cells and after a duration of about 10 minutes in the case of MDA-MB-231 cells.

Example 2

In Vitro Cancer Cell Proliferation and Death Assay

In order to investigate the cytotoxic and proliferation-inhibiting effects of IF1 in cancer cells, an MTT (3-(4,5-dimethylthiazolyl-2)-2,5-diphenyltetrazolium bromide) assay and a CVS (crystal violet solution) assay were performed. MTT and CVS assays are methods of measuring the growth of living cells. MTT uses MTT reduction by mitochondrial reductase of living cells, and CVS measures the viability of cells using a phenomenon in which cells are detached from the plate upon death, whereby a crystal violet staining level decreases.

Each cancer cell line (HepG2, MDA-MB-231, T47D, HeLa) was seeded into a 96-well plate and incubated in an incubator under conditions of 37° C. and 5% $CO_2$ overnight, and was then incubated again in a fresh serum-free medium the next day overnight. The cells were treated with IF1 at each concentration, except for a control group, at 6 h, 24 h, and 48 h (MDA-MB-231 cell line). After treatment with IF1 was completed, the plate was washed twice with PBS, and 200 μl of a mixture of the MTT solution and the medium at a ratio of 1:40 was added to each well. The plate was wrapped with foil to block light, and stored in an incubator under conditions of 37° C. and 5% $CO_2$ until the bottom of the plate turned purple. Then, the MTT solution was removed, 200 μl of DMSO was added to each well, and the well was allowed to stand on a shaker at room temperature for 5 minutes. The solution in each well was transferred to a fresh plate again, and the absorbance was measured at 570 nm through an ELISA reader to calculate relative cell proliferation inhibition with respect to 100% of the control cells.

Figure 2:
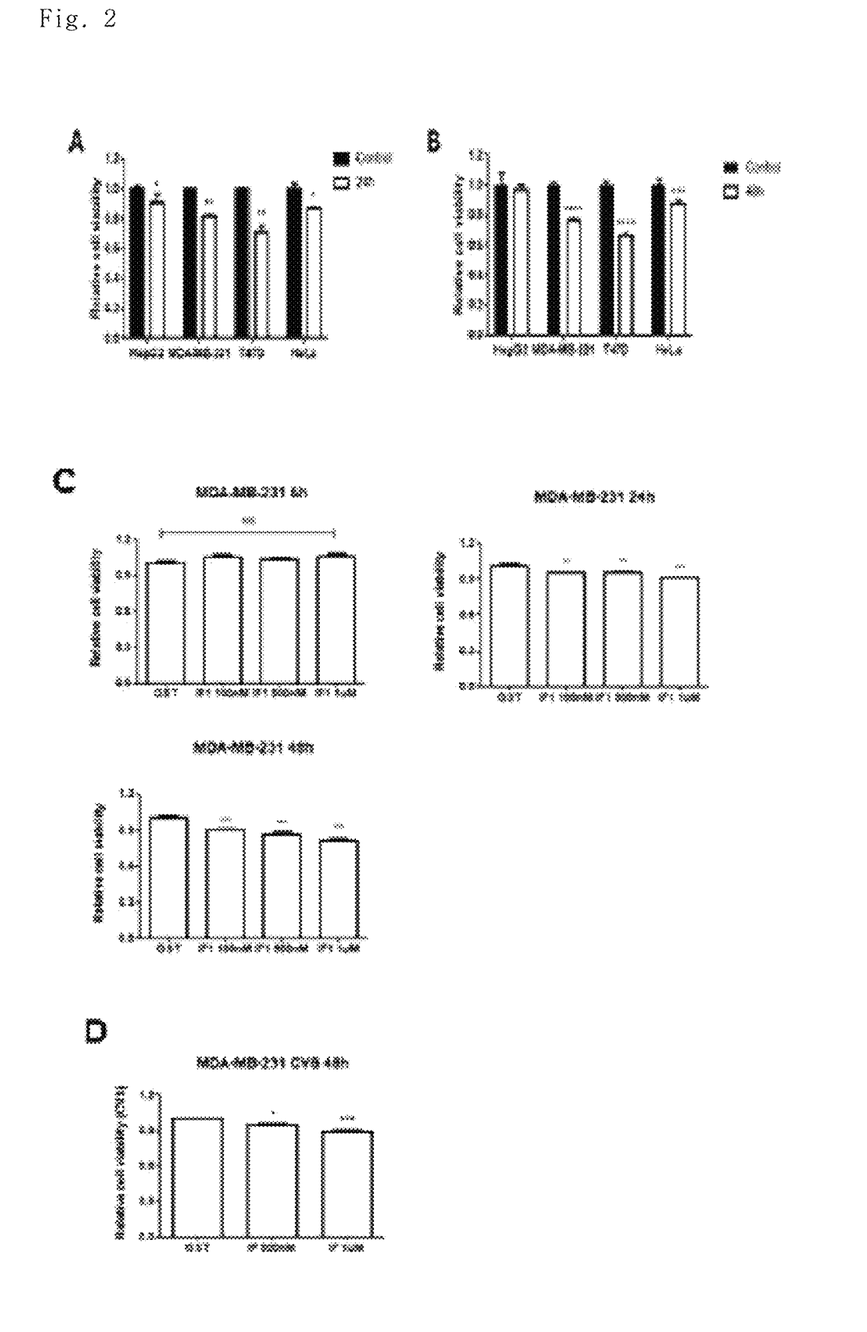
FIG. 2 shows results of MTT and CVS analysis, showing the effect of IF1 treatment on inhibition of the proliferation of four cancer cell lines, wherein (A) and (B) show the results for 4 cell lines by MTT analysis at 24 hours and 48 hours, (C) shows the results of MTT analysis at 6, 24 and 48 hours in MDA-MB-231 breast cancer cell line, and (D) shows the relative cell viability measured at 48 hours upon IF1 treatment using CVS analysis. * P<0.05,  p<0.01, * p<0.001 and *** p<0.0001 are satisfied upon comparison with corresponding control groups.

The result showed that all four types of cancer cell lines (HepG2, MDA-MB-231, T47D, HeLa) exhibited a significant decrease in cell proliferation at 24 h and 48 h due to treatment with IF1 (A and B of FIG. 2). In addition, the MDA-MB-231 breast cancer cell line exhibited a significant decrease in cell proliferation from 24 h to 48 h (C of FIG. 2).

The cell viability of the MDA-MB-231 breast cancer cell line was further evaluated through CVS staining. After 24 hours, the medium was removed, IF1 (500 nM, 1 μM) was added to DMEM medium containing 0.5% FBS, and breast cancer cells inoculated on a 12-well plate were incubated at 37° C. and 5% $CO_2$ for 48 hours. Then, the cells were stained using 25% methanol and a 0.5% crystal violet solution. The cells were washed three times with PBS, and then the absorbance at 570 nm of the solution dissolved in 1% SDS was measured and this was repeated three times to obtain an average.

The result showed that the cell proliferation decreased compared to the control at 48 h in an IF1 concentration-dependent manner (D of FIG. 2).

Example 3

Effect of Treatment with IF1 on Inhibition of Migration of Cancer Cells

Cancer cells in the human body migrate to healthy tissues and cause metastasis through the composition of their characteristics and the microenvironment. Metastasis of cancer cells means the conversion of normal tissues to cancerous tissues. Thus, the effect of IF1 on cancer cells was observed through cell migration experiments.

Each well was scratched in one direction and then MDA-MB-231 cells cultured in a 6-well plate were treated with IF1 at different concentrations, and were observed with an optical microscope at 48 hours.

Figure 3:
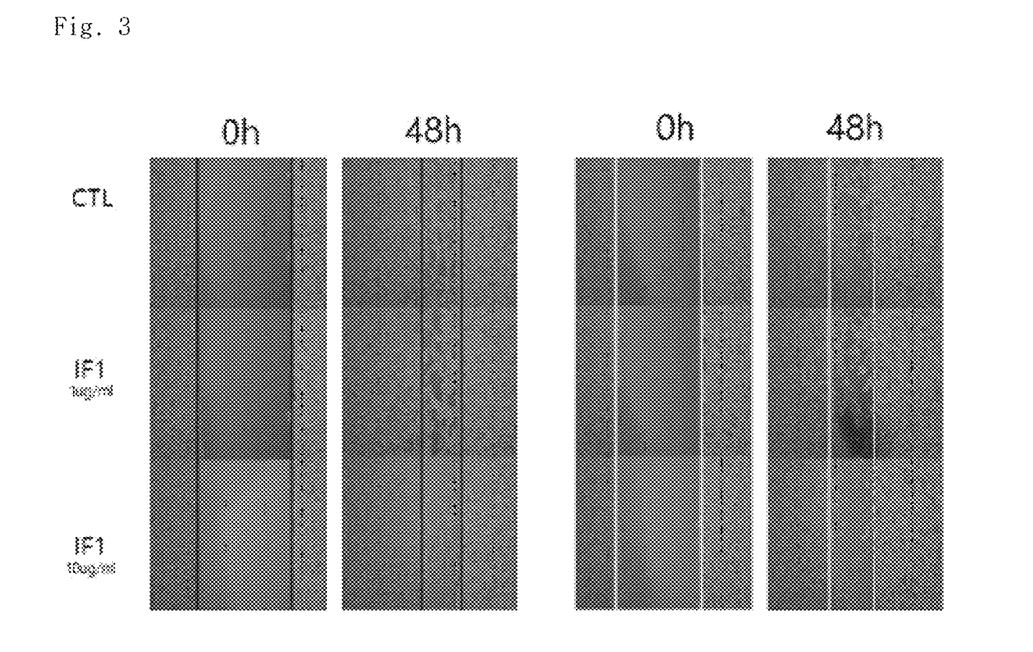
FIG. 3 shows the result of treatment with IF1 (1 ug/ml, 10 ug/ml) for 48 hours upon a migration assay to determine the effect of IF1 treatment on inhibition of migration of cancer cells.

The result showed that as the concentration of IF1 increased, the number of cells that migrated to the empty space decreased, which indicates that IF1 inhibited the migration of cancer cells (FIG. 3).

Example 4

Measurement of Apoptosis

A caspase 3/7 activity test was performed to confirm the relationship between apoptosis and the anticancer effect of IF1. Caspase is a protein that is activated by extracellular and intracellular factors to promote the reaction of enzymes related to apoptosis, and the activity of Caspase 3/7 is a major marker directly linked to apoptosis.

MDA-MB-231 cells inoculated on a 96-well plate were treated with DMEM containing IF1 and 0.5% FBS and cultured for 48 hours. The result was allowed to react at room temperature for 30 minutes using a Caspase-Glo 3/7 assay kit from Promega, and then luminescence was measured using a luminometer.

Figure 4:
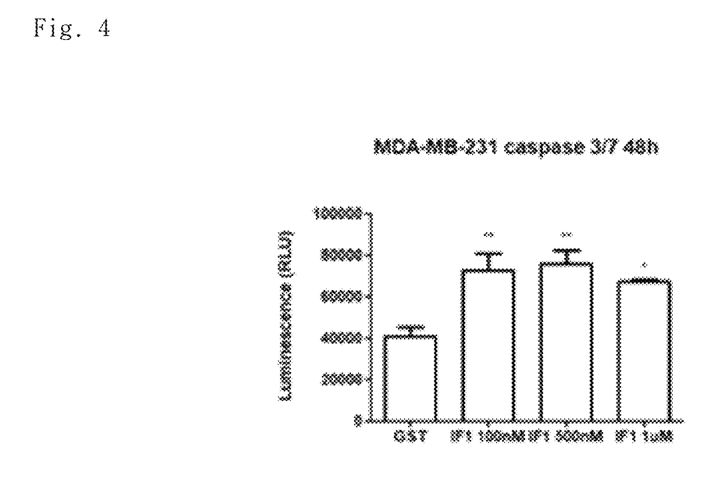
FIG. 4 shows an increase in caspase 3/7 activity, showing the induction of apoptosis by IF1 treatment. * P<0.05,  p<0.01, * p<0.001 and *** p<0.0001 are satisfied upon comparison with each control group.

The result of analysis of the average of data obtained through repeated experimentation showed that treatment with IF1 induces apoptosis by increasing caspase 3/7 activity, thereby reducing the survival of breast cancer cells (FIG. 4).

Example 5

Measurement of Cell Autophagy

In order to confirm the relationship between the anticancer effect of IF1 and autophagy, western blot and MTT assay were performed. mTOR is one of the protein kinases involved in cell growth, and is a major factor related to autophagy. mTOR is regulated within the cell when the cell is in a stressful environment or when the supply of nutrients is difficult. In particular, it is known to be inhibited by the PI3K/AKT signaling pathway, which responds to external stimuli of the cells.

In order to elucidate the correlation between IF1 and autophagy-related factors, phosphorylation and expression levels of S6 (mTOR complex component), AKT, and LC3B proteins were detected by Western blot in the MDA-MB-231 breast cancer cell line.

Figure 5:
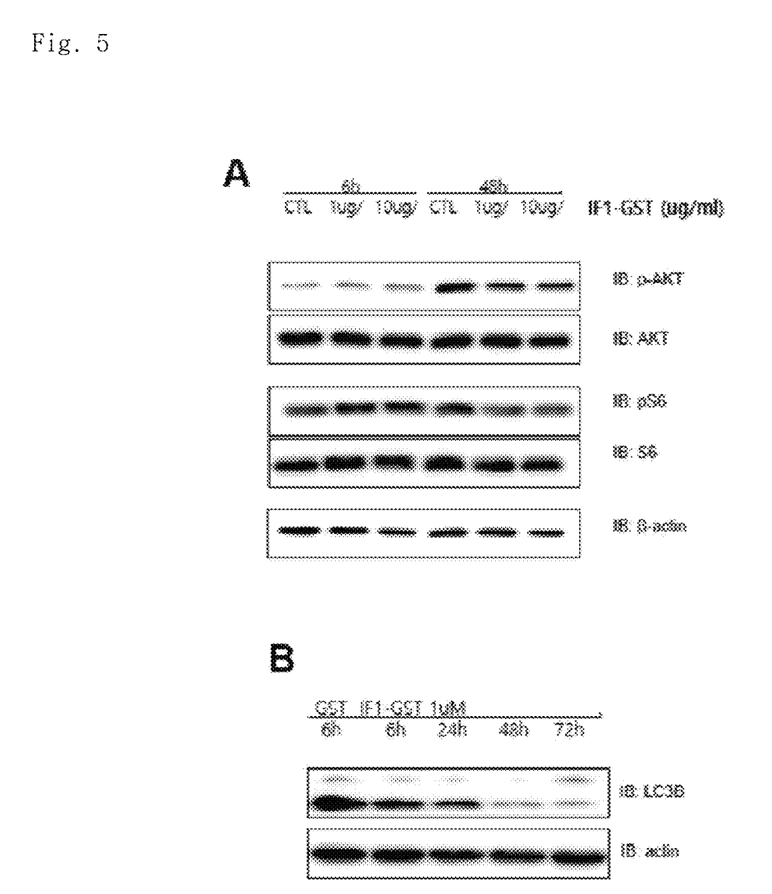
FIG. 5 shows the results of western blot, showing the decrease in (A) Akt and mTOR activity and (B) the expression of LC3B protein by IF1.

The result showed that treatment with IF1 inhibited the phosphorylation of Akt and S6 proteins after 48 hours, thereby lowering the activity thereof (A of FIG. 5). It was also observed that the expression level of LC3B, an autophagy marker, decreased (B of FIG. 5).

In addition, in order to observe the effect of autophagy on the anticancer activity of IF1, the MDA-MB-231 breast cancer cell line was simultaneously treated with IF1 and LY294002, an inhibitor of PI3K/AKT, in the MTT assay conducted in Example 1.

Figure 6:
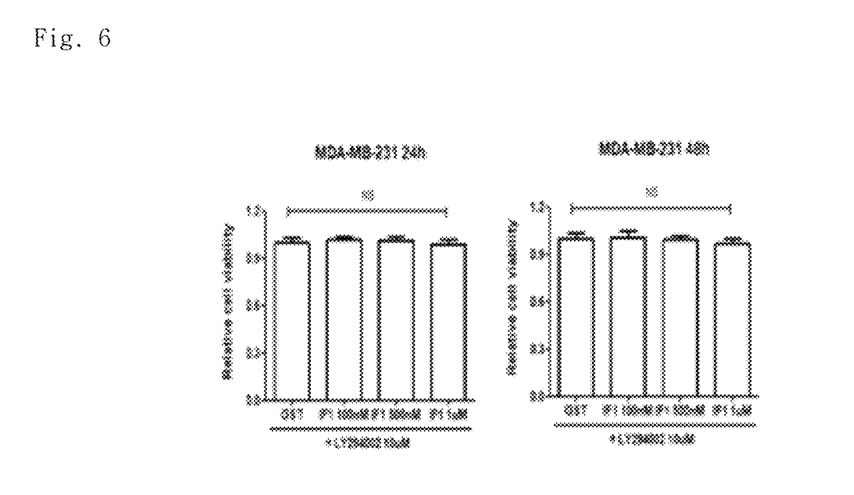
FIG. 6 shows determination of cell proliferation inhibition and apoptosis effects of IF1 through PI3K using a PI3K inhibitor.

The result showed that treatment with LY294002 effectively inhibited the anticancer activity of IF1, which indicates that the autophagy activity by mTOR regulation is the target of the signaling pathway of IF1 (FIG. 6).

Example 6

Induction of ER Stress by Treatment With IF1

The ER (endoplasmic reticulum) is an organelle that plays an important role in maintaining homeostasis by being responsible for folding, modification and transport of intracellular proteins. Recently, it is known to induce apoptosis and autophagy, when ER stress occurs in cancer cells and thus is attracting attention. The induction of ER stress causes anticancer activity through UPR (unfolded protein response). At this time, signaling is realized by a phenomenon in which XBP1 is cleaved by RNase action and is thereby converted to sXBP1.

Figure 7:
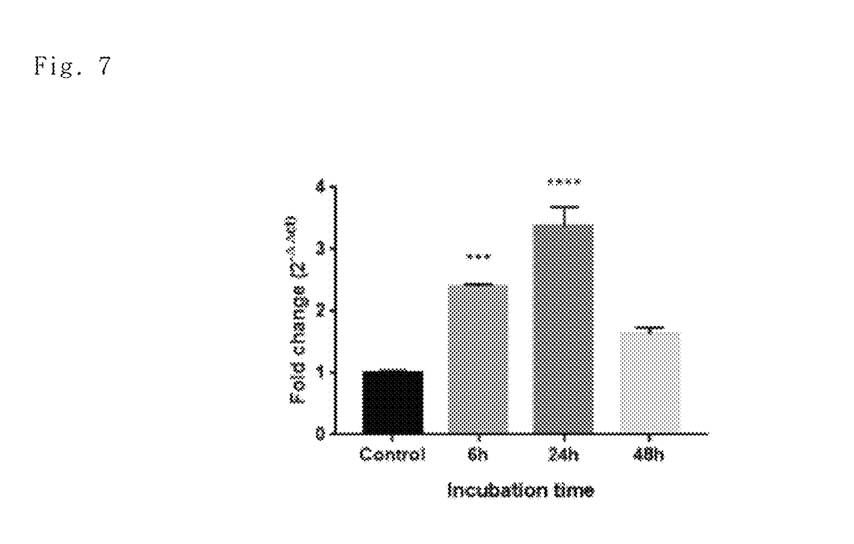
FIG. 7 shows the expression level of sXBP1, indicating the induction of ER stress by IF1. * P<0.05,  p<0.01, * p<0.001 and **** p<0.0001 are satisfied upon comparison with each control group.

Accordingly, in order to determine the relationship between IF1 and ER stress, the MDA-MB-231 breast cancer cell line was treated with IF1 for 6 h, 24 h, and 48 h to observe the mRNA expression level of sXBP1 (FIG. 7).

The result showed that the expression of sXBP1 was significantly increased compared to the control group at 6 h and 24 h, which indicates that the anticancer effect of IF1 is related to ER stress.

INDUSTRIAL APPLICABILITY

The IF1 (ATPase inhibitory factor 1) according to the present invention has effects of inhibiting proliferation of cancer cells, increasing extracellular ATP release, suppressing migration of cancer cells, and inducing apoptosis or autophagy of cancer cells in a variety of cancer cells, and thus exhibits anti-cancer activity or activity of inhibiting cancer metastasis, thus being very useful as a potent active ingredient of anti-cancer drugs.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

SEQUENCE LISTING FREE TEXT

An electronic file is attached.

The invention claimed is:

1. A method for preventing, or treating cancer or inhibiting cancer metastasis comprising administering IF1 (ATPase inhibitory factor 1) as an active ingredient to a subject in need thereof;
   wherein the cancer is liver cancer or cervical cancer.

2. The method according to claim 1, wherein said IF1 is administered with a pharmaceutically acceptable carrier, excipient or diluent.

* * * * *

```
                          SEQUENCE LISTING

<160> NUMBER OF SEQ ID NOS: 1

<210> SEQ ID NO 1
<211> LENGTH: 81
<212> TYPE: PRT
<213> ORGANISM: Artificial Sequence
<220> FEATURE:
<223> OTHER INFORMATION: Recombinant IF1

<400> SEQUENCE: 1

Val Ser Asp Ser Ser Asp Ser Met Asp Thr Gly Ala Gly Ser Ile Arg
1               5                   10                  15

Glu Ala Gly Gly Ala Phe Gly Lys Arg Glu Lys Ala Glu Glu Asp Arg
            20                  25                  30

Tyr Phe Arg Glu Lys Thr Lys Glu Gln Leu Ala Ala Leu Arg Lys His
            35                  40                  45

His Glu Asp Glu Ile Asp His His Ser Lys Glu Ile Glu Arg Leu Gln
    50                  55                  60

Lys Gln Ile Glu Arg His Lys Lys Lys Ile Gln Gln Leu Lys Asn Asn
65                  70                  75                  80

His
```